United States Patent
Lamb

(10) Patent No.: US 7,220,782 B1
(45) Date of Patent: *May 22, 2007

(54) METHODS TO REDUCE THE SENSITIVITY OF ENDOTHELIALLY-COMPROMISED VASCULAR SMOOTH MUSCLE

(75) Inventor: Fred S. Lamb, Solon, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 509 days.

This patent is subject to a terminal disclaimer.

(21) Appl. No.: 09/512,926

(22) Filed: Feb. 25, 2000

Related U.S. Application Data

(60) Provisional application No. 60/121,727, filed on Feb. 26, 1999.

(51) Int. Cl.
*A61K 31/135* (2006.01)

(52) U.S. Cl. .................. 514/648; 514/649; 514/651

(58) Field of Classification Search ................ 514/324
See application file for complete search history.

(56) References Cited

U.S. PATENT DOCUMENTS

| | | | | |
|---|---|---|---|---|
| 5,077,601 | A | 12/1991 | Hatada et al. | 357/81 |
| 5,224,538 | A | 7/1993 | Jacoby | 165/166 |
| 5,470,883 | A * | 11/1995 | Stromberg | 514/648 |
| 5,472,985 | A | 12/1995 | Grainger et al. | 514/651 |
| 5,658,936 | A * | 8/1997 | Kifor et al. | 514/381 |
| 5,691,355 | A | 11/1997 | Bryant et al. | 514/324 |
| 5,760,066 | A | 6/1998 | Tang | 514/378 |
| 5,770,609 | A | 6/1998 | Grainger et al. | 514/319 |
| 5,795,898 | A | 8/1998 | Brown et al. | 514/263 |
| 5,811,447 | A | 9/1998 | Kunz et al. | 514/411 |
| 5,912,805 | A | 6/1999 | Freuler et al. | 361/705 |
| 5,940,267 | A | 8/1999 | Ko et al. | 361/699 |
| 5,957,194 | A | 9/1999 | Azar | 165/80.3 |
| 6,015,008 | A | 1/2000 | Kogure et al. | 165/185 |
| 6,054,198 | A | 4/2000 | Bunyan et al. | 428/40.5 |
| 6,197,789 | B1 * | 3/2001 | Grainger et al. | 514/319 |

FOREIGN PATENT DOCUMENTS

WO 96/40098 12/1996

OTHER PUBLICATIONS

Andreas, S., et al., "Characterization of cell volume-sensitive chloride currents in freshly prepared and cultured pancreatic acinar cells from early postnatal rats", *J. of Physiology*, 513 (2), 453-465, (Dec. 1, 1998).

Borsani, G., et al., "Characterization of a Human and Murine Gene (CLCN3) Sharing Similarities to Voltage-Gated Chloride Channels and to a Yeast Integral Membrane Protein", *Genomics*, 27, pp. 131-141, (1995).

Dick, G.M., et al., "Functional and molecular identification of a novel chloride conductance in canine colonic smooth muscle", *Am. J. of Physiology*, 275 (4), Part 1, C940-C950, (Oct. 1998).

Duan, D., et al., "Molecular identification of a volume-regulated chloride channel", *Nature*, 390, pp. 417-421, (Nov. 1997).

Kawasaki, M., et al., "Stable and Functional Expression of the ClC-3 Chloride Channel in Somatic Cell Lines", *Neuron*, 14, pp. 1285-1291, (Jun. 1995).

Lamb, F.S., "Supplemental Data to 1R01 18L62483-01 ClC-3 Chloride Ion Channels in Vascular Smooth Muscle", *PHS 398 (Rev. May 1995)*, 4 p., (May 1998).

Lamb, F.S., et al., "Chloride ion currents contribute functionally to norepinephrine-induced vascular contraction", *Am. J. Physiol.*, 275, pp. H151-H160, (1998).

Lamb, F.S., et al., "The endothelium modulates the contribution of chloride currents to noreponephrine-induced vascular contraction", *Am. J. Physiol.*, 275, H161-H168, (1998).

Liu, B., et al., "Tamoxifen Normalizes the Increase in Vascular Sensitivity Associated with Endothelial Disruption", *FASEB Journal*, 13 (4), Part 1, Abstract, p. A49, (Mar. 12, 1999).

Qiu, X.C., et al., "The cardiovascular reactions mediated by TPA and tamoxifen in spinal cord of conscious rats", *Yaoxue Xuebao*, 30 (7), 481-485, (1995).

Yamazaki, J., et al., "Functional and Molecular expression of volume-regulated chloride channels in canine vascular smooth muscle cells", *J. of Physiology*, 507 (3), 729-736, (Mar. 15, 1998).

Owens "Regulation of Differentiation of Vascular Smooth Muscle Cells," *Physiological Reviews*, 1995, 75:487-517.

Ralph, D. J., et al., "The Treatment of Payronie's Disease with Tamoxifen", *British Journal of Urology*, 70, Abstract, Database EMBASe on ACS. Accession No. 93001761 (1992) 648-651.

* cited by examiner

*Primary Examiner*—Sreeni Padmanabhan
*Assistant Examiner*—Jennifer Kim
(74) *Attorney, Agent, or Firm*—Viksnins Harris & Padys PLLP

(57) ABSTRACT

The present invention discloses materials and methods useful to treat sensitivity of endothelially-compromised vascular smooth muscle. In one embodiment, CLC3 blockers, particularly compounds of the Formula I are used to treat sensitivity.

8 Claims, 3 Drawing Sheets

METHODS TO REDUCE THE SENSITIVITY OF ENDOTHELIALLY-COMPROMISED VASCULAR SMOOTH MUSCLE

This application claims priority to Provisional Patent Application 60/121,727 filed Feb. 26, 1999.

FIELD OF THE INVENTION

The present invention relates generally to the field of chemical agents affecting the vasculature. In particular, this invention contributes to the study of the affects of chemical agents in diseased, mechanically disrupted or genetically abnormal vasculature.

BACKGROUND OF THE INVENTION

Vascular smooth muscle (herein referred to as "VSM") in the normal state is covered by an endothelial layer of cells as indicated in FIG. 1. In the normal state, VSM contracts in response to vasoconstrictor agonists, including norepinephrine. Lamb and Barna, 275 Am J Physiol H151 (1998). Disruption of the endothelial layer has been shown to increase sensitivity to these agonists. These findings are consistent with studies which showed that changes in the basal production of nitric oxide alters VSM responsiveness to vasoconstrictors. Joulow-Schaeffer et al., 259 Am J Physiol R38 (1990); Rees et al., 86 Proc Natl Acad Sci USA 3375 (1989); Wiklund et al., 185 Eur J Pharmacol 123 (1990).

Chloride ion channels are present in VSM (Klockner 424 Pflugers Arch 231 (1991); Lamb et al., 75 Circ Res 742 (1994)) and have been shown to be activated by vasoconstrictor agonists (Klockner and Isenberg, 418 Pflugers Arch 168 1991); Pacaud et al., 97 Br J Pharmacol 139 (1989)). Chloride ion currents have also been shown to contribute functionally to norepinephrine-induced contraction of normal vasculature. Lamb and Barna, 275 Am J Physiol H151 (1998). In that study, tamoxifen was shown to have no effect on the norepinephrine-induced contraction of normal vasculature (vasculature with intact endothelium). In Lamb and Barna, 275 Am J Physiol H161 (1998), the endothelium was shown to modulate the contribution of the chloride currents to norepinephrine-induced VSM constriction. The effects of tamoxifen on endothelium-compromised tissue was not studied, since no effect was seen in normal tissues. In other studies, a particular chloride ion channel, "CLC3", was shown to be responsible for swelling-induced chloride conductance. Duan et al., 390 Nature 417 (1997). Tamoxifen was shown to block the ion channel responsible for swelling-induced chloride conductance, a result which had previously been demonstrated. Nilius et al., 428 Pflugers Arch 364 (1994).

The effects of tamoxifen on estrogen levels, and concomitant effects on other systems, including NE and dopamine expression, have also been studied. Kocsis et al., Vol. 69, Br J Exp Path 157 (1988); Etgen and Petitti, 49(6) J Neurochem 1732 (1987); Baksi et al., 20 Neuropharm 1163 (1981). Moreover, a method for treating peripheral vasoconstriction with tamoxifen citrate has been disclosed in U.S. Pat. No. 5,470,883. In that patent, the anti-estrogen effects of tamoxifen were said to be responsible for reducing the peripheral vasoconstriction of exogenously-administered adrenergic compound.

Vascular smooth muscle can be damaged by mechanical or physiological means. Medical procedures, such as balloon angioplasty, disease-induced or genetically-influenced pathogies, such as diabetes and hypertension, create risk or predisposal for endothelial damage. In addition, endothelial damage in itself may exacerbate these pathologic processes and contribute to symptoms which are associated with them. For instance, coronary artery disease results in localized endothelial damage, and sudden surges in natural vasoconstrictors (such as NE) can cause heart failure. Previous treatments for these endothelially-compromised patients have been limited to chemicals agents which cause system-wide VSM relaxation, and consequently, frequently cause side effects such as orthostasis (dizziness) due to transient low blood pressure during certain activities.

SUMMARY OF THE INVENTION

In general, the present invention provides methods to reduce the sensitivity of endothelially-compromised vascular smooth muscle. In certain embodiments, methods are herein provided to influence blood pressure, in a tissue-selective manner, by administering a ClC3 blocker. In contrast to previous agents which cause patients to have system-wide vascular smooth muscle relaxation, it is now possible to affect only the pathologic vascular smooth muscle. In other words, use of CLC3 blockers allows for tissue-targeting in a highly specific and reliable manner, which results in avoidance of the unpleasant side effects of system-wide vasodilation associated with previously-known treatments.

The present invention provides methods to reduce the sensitivity of endothelially-compromised vascular smooth muscle in a patient in need of such reduction, comprising administering a pharmaceutically effective amount of a CLC3 blocker. Preferred are methods to reduce the sensitivity of endothelially-compromised vascular smooth muscle, comprising administering a compound of Formula I

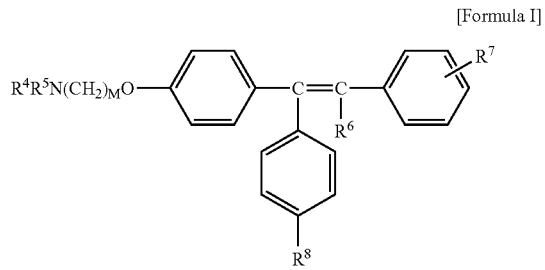

[Formula I]

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof.

A most preferred embodiment of these methods are those wherein the compound administered is 1-p-β-dimethylami noethoxyphenyl-trans-1,2-diphenylbut-1-ene (tamoxifen), or a pharmaceutically acceptable salt thereof.

Tamoxifen has the chemical structure:

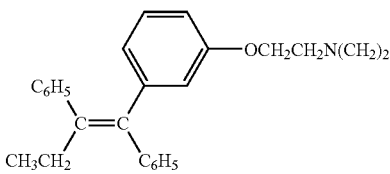

Also provided are methods to ameliorate the negative effects associated with vascular smooth muscle endothelium damage in a patient is need of such treatment, comprising administering a pharmaceutically-effective amount of a CLC3 blocker, or a pharmaceutically acceptable salt thereof. Preferred are methods as described, comprising administering a pharmaceutically effective amount of a compound of Formula I

[Formula I]

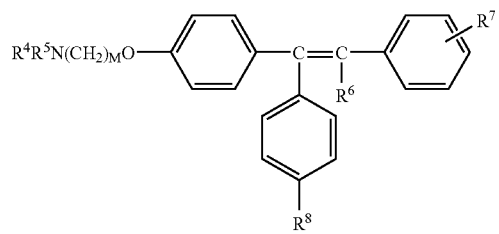

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof.

Methods as described, wherein said endothelium damage is the result of diabetes, surgical procedure, coronary artery disease or hypertension are preferred. Methods which further comprise administering a pharmaceutically-effective compound selected from the group consisting of: an anti-hypertension agent; an anti-diabetes agent; and anti-coronary artery disease agent; and an anti-restenosis agent are also preferred.

In another embodiment, there are provided methods to affect chloride ion channel 3 receptors comprising administering a compound of Formula I

[Formula I]

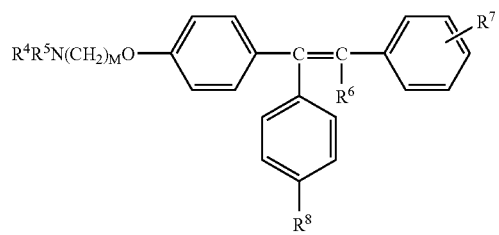

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof.

Preferred are methods as described, wherein the compound administered is 1-p-β-dimethylaminoethoxyphenyl-trans-1,2-diphenylbut-1-ene (tamoxifen), or a pharmaceutically acceptable salt thereof.

In yet another embodiment, there are provided methods to reduce contraction of endothelially-compromised vascular smooth muscle in response to a vasoconstrictive agent, comprising administering a chloride ion channel 3 blocker, or a salt thereof. A method as described, wherein the chloride ion channel 3 blocker is a compound of Formula I

[Formula I]

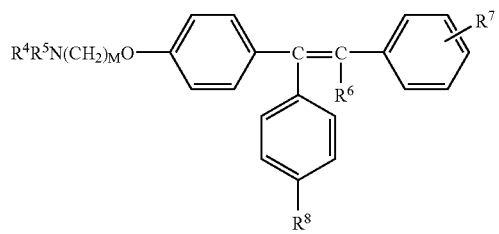

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof, is preferred.

Most preferred are methods as described, wherein the compound administered is 1-p-β-dimethylaminoethoxyphenyl-trans-1,2-diphenylbut-1-ene (tamoxifen), or a pharmaceutically acceptable salt thereof. Methods as described, wherein the agonist is NE, are preferred.

Also provided are methods to decrease the effects of vasoconstrictors in pathologic tissues and not in non-pathologic tissues in a patient with pathologic tissues, and who is in need of such decrease, comprising administering a pharmaceutically-effective amount of a CLC3 blocker, or a pharmaceutically acceptable salt thereof. Methods as described, wherein the CLC3 blocker is a compound of Formula I, wherein the CLC3 blocker is a compound of Formula I

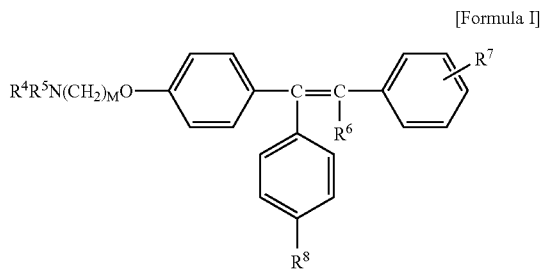

[Formula I]

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof, are preferred.

Moreover, methods as described, wherein the compound administered is 1-p-β-dimethylaminoethoxyphenyl-trans-1,2-diphenylbut-1-ene (tamoxifen), or a pharmaceutically acceptable salt thereof, is more preferred.

In another embodiment of the present invention, there are provided methods to stabilize blood pressure in patients with endothelium-compromised vascular smooth muscle, and who are in need of such stabilization, comprising administering a pharmaceutically-effective amount of a CLC3 blocker. Methods wherein the CLC3 blocker is a compound of Formula I

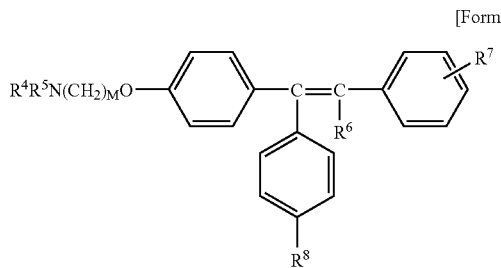

[Formula I]

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof, are preferred.

Methods as described, wherein the CLC3 blocker is a compound of Formula I, or a pharmaceutically acceptable salt thereof, are preferred. More preferred are methods wherein the compound administered is 1-p-β-dimethylaminoethoxyphenyl-trans-1,2-diphenylbut-1-ene (tamoxifen), or a pharmaceutically acceptable salt thereof.

Definitions:

"a" or "an", when describing a noun, refers to one or more of that noun.

"agent" means any compound or composition made by any means. "Agent" includes synthetic or naturally-occurring compounds or compositions, whether purified or not, and can include: herbal extract(s); precursor(s); metabolite(s); and ingredient(s), including enantiomer(s) of a racemic mixture. The definition of "agent" includes any compound or composition as described in this paragraph, which has been shown to be active for the desired medical purpose, including any agent which works to affect a desired medical result, and/or is approved by the US Food & Drug Administration, or foreign equivalent.

"anti-coronary artery disease agent" means any agent which causes reduction in the effects of coronary artery disease, and/or which is considered by the medical or scientific community, or the general public, to reduce coronary artery disease or the symptoms associated with coronary artery disease.

"anti-diabetes agent" means any agent which causes reduction in diabetes, and/or which is considered by the medical or scientific community, or the general public, to reduce diabetes or the symptoms associated with diabetes.

"anti-hypertension agent" means any agent which causes reduction in hypertension, and/or which is considered by the medical or scientific community, or the general public, to reduce hypertension or the symptoms associated with hypertension.

"anti-restenosis" means any agent which causes reduction in restenosis, and/or which is considered by the medical or scientific community, or the general public, to reduce restenosis or the symptoms associated with restenosis.

"CLC3" means chloride ion channel 3, and has the same meaning as CLC-3.

"damage" means any reduction in physiological or structural function, whether caused by mechanical, chemical or other means. The standard for determining whether function is "reduced" is determined by comparing the state of being in question to either population normals or individual normals. Moreover, if CLC3 blockers, in particular, tamoxifen or tamoxifen analogues are able to decrease vascular sensitivity to agonists in the patient, "damage" is assumed.

"effective amount" means that dosage of active compound(s) sufficient to provide therapeutic treatment of the specified medical indication.

"patient" means any living organism with vascular smooth muscle.

"surgical procedure" means any medical procedure requiring mechanical or mechanical/chemical manipulation of a patient's body, wherein said procedure results in damage to the endothelium layer adjoining vascular smooth muscle.

DETAILED DESCRIPTION OF THE INVENTION

Figure 1:
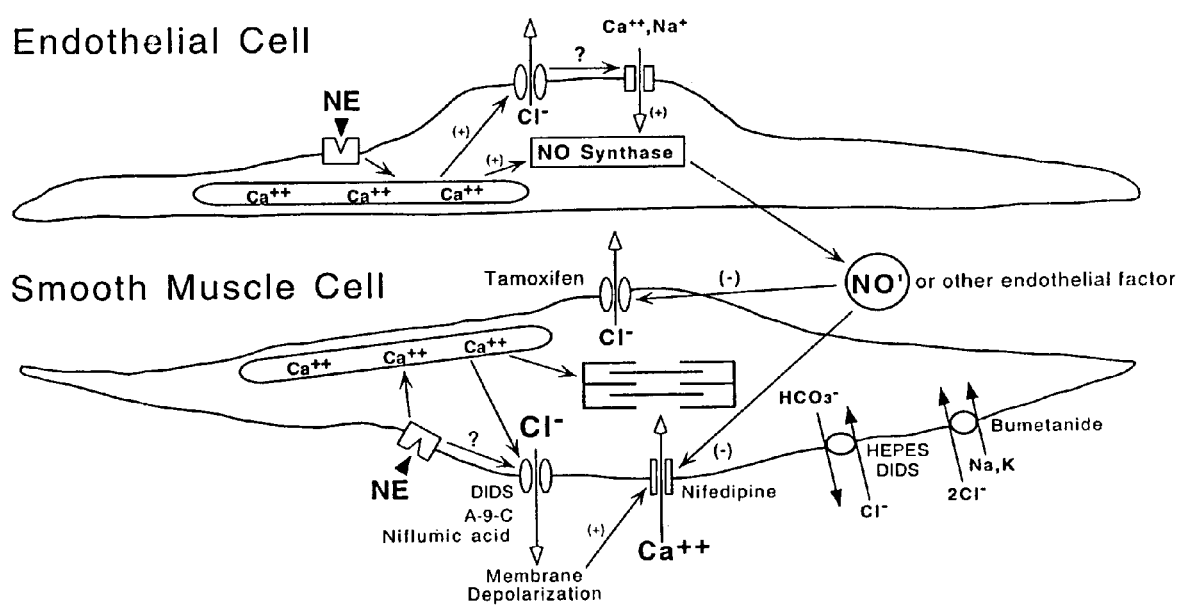
FIG. 1: Diagram of normal blood vessel surface layers.

The present invention provides methods to reduce the sensitivity of endothelially-compromised vascular smooth muscle in a patient in need of such reduction, comprising administering a pharmaceutically effective amount of a CLC3 blocker, or a pharmaceutically-acceptable salt thereof. Methods as described, wherein the CLC3 blocker is a compound of Formula I

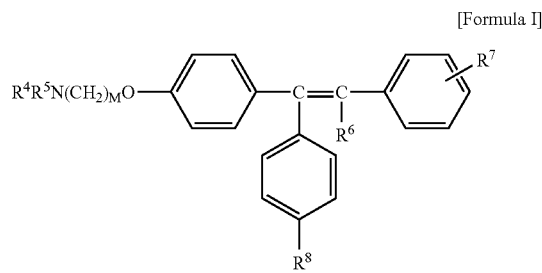

[Formula I]

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof, are preferred.

A more preferred embodiment of these methods are those wherein the compound administered is 1-p-β-dimethylaminoethoxyphenyl-trans-1,2-diphenylbut-1-ene(tamoxifen), or a pharmaceutically acceptable salt thereof.

Also provided are methods to ameliorate the negative effects associated with vascular smooth muscle endothelium damage in a patient is need of such amelioration, comprising administering a pharmaceutically effective amount of a CLC3 blocker, or a pharmaceutically acceptable salt thereof. Methods as described, wherein the CLC3 blocker is a compound of Formula I, are preferred. More preferred are methods as described, wherein the compound administered is tamoxifen, or a pharmaceutically-acceptable salt thereof. Methods as described, wherein said endothelium damage is the result of diabetes, surgical procedure, coronary artery disease, or hypertension are also preferred. Methods which further comprises administering a pharmaceutically-effective compound selected from the group consisting of: an anti-hypertension agent; an anti-diabetes agent; an anti-coronary artery disease agent; and an anti-restenosis agent are also preferred.

In another embodiment, there are provided methods to affect CLC3 receptors comprising administering a compound of Formula I, or a pharmaceutically acceptable salt thereof. Preferred are methods as described, wherein the compound administered is 1-p-β-dimethylaminoethoxyphenyl-trans-1,2-diphenylbut-1-ene (tamoxifen), or a pharmaceutically acceptable salt thereof.

In yet another embodiment, there are provided methods to reduce contraction of endothelially-compromised vascular smooth muscle in response to a vasoconstrictive agent, comprising administering a CLC3 blocker, or a salt thereof. Methods as described, wherein the CLC3 blocker is a compound of Formula I, or a pharmaceutically acceptable salt thereof are preferred. More preferred are methods as described, wherein the compound administered is 1-p-β-dimethylaminoethoxyphenyl-trans-1,2-diphenylbut-1-ene (tamoxifen), or a pharmaceutically acceptable salt thereof. Methods as described, wherein the agonist is NE, are preferred.

Also provided are methods to decrease the effects of vasoconstrictors in pathologic tissues and not in non-pathologic tissues, in a patient with pathologic tissues and who is in need of such decrease, comprising administering a pharmaceutically-effective amount of a CLC3 blocker, or a pharmaceutically acceptable salt thereof. Methods as described, wherein the CLC3 blocker is a compound of Formula I, or a pharmaceutically acceptable salt thereof, are preferred.

Moreover, methods as described, wherein the compound administered is 1-p-β-dimethylaminoethoxyphenyl-trans-1,2-diphenylbut-1-ene (tamoxifen), or a pharmaceutically acceptable salt thereof, is more preferred.

In another embodiment of the present invention, there are provided methods to stabilize blood pressure in patients with endothelium-compromised vascular smooth muscle, and who are in need of such stabilization, comprising administering a pharmaceutically-effective amount of a CLC3 blocker, or a pharmaceutically acceptable salt thereof. Methods as described, wherein the CLC3 blocker is a compound of Formula I, or a pharmaceutically acceptable salt thereof, are preferred. More preferred are methods wherein the compound administered is 1-p-β-dimethylaminoethoxyphenyl-trans-1,2-diphenylbut-1-ene (tamoxifen), or a pharmaceutically acceptable salt thereof.

The descriptive chemical terms used with Formula I have their usual meaning. For example, the term "halo" includes bromo, chloro, fluoro, and iodo. The term "lower alkyl" or "$C_1$–$C_4$ alkyl" refers to the straight and branched aliphatic radicals of 1–4 carbon atoms including methyl, ethyl, propyl, isopropyl, n-butyl, isobutyl, sec-butyl, and tert-butyl. In addition, the term "substituted phenyl" refers to a phenyl molecule having one or two substituents selected from the group consisting of $C_1$–$C_4$ alkyl, $C_1$–$C_5$ alkoxy, hydroxy, nitro, chloro, fluoro, or tri(chloro or fluoro)methyl. Finally, the term "$C_1$–$C_4$ alkoxy" includes the straight and branched aliphatic ether radicals of 1–4 carbon atoms such as methoxy, ethoxy, propoxy, isopropoxy, n-butoxy, isobutoxy, sec-butoxy, and tert-butoxy.

A preferred Formula I compound, in which $R^4$ and $R^5$ each are methyl, $R^6$ is ethyl, $R^7$ and $R^8$ each are H, and n is 2, is known in the art as tamoxifen. Tamoxifen and its analogs are most well known as antiestrogen compounds and tamoxifen primarily is used for the treatment of breast carcinoma in women. See, *The Merk Index,* 11th Ed., 1430 (1989). Tamoxifen citrate (Nolvadex.®., Zeneca Pharmaceuticals, Wilmington, Del. 19897) is a trans-isomer of a triphenylethylene derivative. Tamoxifen citrate has a molecular weight of 563.62, the pKa is 8.85, the equilibrium solubility in water at 37 degrees C. is 0.5 mg/mL, and in 0.002N. HCl at 37 degrees C., it is 0.2 mg/mL.

For therapeutic treatment of the specified indications, compounds of the present composition, particularly a Formula I compound, can be compounded and formulated into pharmaceutical compositions in unit dosage form for parenteral, transdermal, rectal, nasal, intravenous administration or, preferably, oral administration. Such pharmaceutical compositions are prepared in a manner well known in the art and comprise a Formula I compound, optionally including an additional compound. In making the compositions of the present invention, the active ingredients will usually be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Additionally, compounds of the present composition, particularly Formula I compounds, are well suited to formulation as sustained release dosage forms and the like. The formulations can be so construed that they release the active ingredient only or preferably in a particular physiological location, possibly over a period of time. The coatings, envelopes, and protective matrices may be made, for example, from polymeric substances or waxes.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The compositions can additionally include lubricating agents, wetting agents, emulsifying and suspending agents, preserving agents, sweetening agents or flavoring agents. The compositions may be formulated so as to provide quick, sustained, or delayed release of the active ingredient(s) after administration to the patient by employing procedures well known in the art. For oral administration, a compound optionally including a second component compound, can be admixed with carriers and diluents molded into tablets or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient(s). The term "unit dosage form" refers to physically discreet units suitable as unitary dosages for human subjects, each unit containing a predetermined quantity of active ingredients calculated to produce the desired therapeutic effect, in association with the required pharmaceutically acceptable carrier. By "pharmaceutically acceptable", it is meant the carrier, diluent, or excipient must be acceptable with the other ingredients of the formulation and not deleterious to the recipient thereof.

Compounds of the present invention, can be formulated alone or in combination with another pharmaceutical agent, and can generally will be administered in a convenient formulation. The following formulation examples only are illustrative and are not intended to limit the scope of the present invention.

| Formulations | |
|---|---|
| Ingredient | Quantity (mg/capsule) |
| Formulation 1: Gelatin Capsules Hard gelatin capsules are prepared using the following: | |
| Formula I compound | 0.1–1000 |
| Starch, NF | 0–650 |
| Starch flowable powder | 0–650 |
| Silicone fluid 350 centistokes | 0–15 |
| Formulation 2: Formula I capsule | |
| Formula I compound | 1 |
| Starch, NF | 112 |
| Starch flowable powder | 225.3 |
| Silicone fluid 350 centistokes | 1.7 |
| Formulation 3: Formula I capsule | |
| Formula I compound | 5 |
| Starch, NF | 108 |
| Starch flowable powder | 225.3 |
| Silicone fluid 350 centistokes | 1.7 |
| Formulation 4: Formula I capsule | |
| Formula I compound | 10 |
| Starch, NF | 103 |
| Starch flowable powder | 225.3 |
| Silicone fluid 350 centistokes | 1.7 |
| Formulation 5: Formula I capsule | |
| Formula I compound | 50 |
| Starch, NF | 150 |
| Starch flowable powder | 397 |
| Silicone fluid 350 centistokes | 3.0 |

The specific formulations above may be changed in compliance with the reasonable variations provided, and can include other pharmaceutically-active agents, such as those used to treat hypertension, diabetes, coronary artery disease and restenosis.

A tablet formulation is prepared using the ingredients below:

| Formulation 6: Tablets | |
|---|---|
| Ingredient | Quantity (mg/tablet) |
| Formula I compound | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 25–1000 mg of a formula I compound are made up as follows:

| Formulation 7: Tablets | |
|---|---|
| Ingredient | Quantity (mg/tablet) |
| Formula I compound | 25–1000 |
| Starch | 45 |
| Cellulose, microcrystalline | 35 |
| Polyvinylpyrrolidone (as 10% solution in water) | 4 |

-continued

Formulation 7: Tablets

| Ingredient | Quantity (mg/tablet) |
| --- | --- |
| Sodium carboxymethyl cellulose | 4.5 |
| Magnesium stearate | 0.5 |
| Talc | 1 |

The Formula I compound, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 500.degree.-60.degree. C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 25–1000 mg of medicament per 5 ml dose are made as follows:

Formulation 8: Suspensions

| Ingredient | Quantity (mg/5 ml) |
| --- | --- |
| Formula I compound | 25–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Diagnosis of hypertension, diabetes, restenosis, coronary artery disease or other endothelium-compromised vascular smooth muscle states is within skill of the art, and is evidenced by the internal medicine textbook, such as Harrison's.

Determination whether a compound is a CLC3 blocker can be accomplished according to the Examples herein described.

The compounds can be purchased from commercial sources, such as Sigma Chemical, St. Louis, Mo. However, one skilled in the art is aware how to synthesize these compounds de novo using conventional methods. In particular, compounds of Formula I can be prepared according to the procedures described in U.S. Pat. No. 4,623,600, which patent is hereby incorporated by reference. Pharmaceutically acid addition salts can be prepared according to the disclosure in U.S. Pat. No. 5,691,355, which patent is hereby incorporated by reference.

EXAMPLES

In studies by the present inventors, it was discovered that DIDS (4,4'-diisothiocyanato stilbene-2,2'disulphonic acid) and niflumic acid significantly inhibited the contractile response to ED80 concentrations of norepinephrine (NE) or potassium chloride (KCl) in isolated rings of rat aorta with an intact endothelium. Significantly, tamoxifen did not alter these responses. These vasodilator effects of DIDS and niflumic acid (in the presence of NE or KCl) were endothelium-independent, because they persisted in epithelium-denuded blood vessel segments. The effect of tamoxifen on denuded blood vessel segments was not studied, since no effect was apparent in intact vessels. The above experiments were reported in Lamb and Barna, 275 *Am J Physiol* H151 (1998) and Lamb and Barna, 275 *Am J Physiol* H161 (1998), and are incorporated herein by reference.

Example 1

Assay Materials and Methods

Adult male Sprague-Dawley rats (250–300 g) were obtained from Harlan Sprague Dawley. The animals were killed by exposure to 100% $CO_2$ for 5 minutes, followed by cervical dislocation. Thoracic aortas were removed, cleaned of adherent connective tissue, and cut into 6 mm rings. The endothelium was left intact, and the rings were mounted in individual 10-ml isolated organ chambers using standard methods for recording of isometric tension. Contractile responses were recorded with an eight-channel MacLab8E and stored on a Power Macintosh 7200 computer. passive stretch was set at 2.5 g, and the rings were allowed to equilibrate in physiological salt solution (PSS) at 37° C. for 120 minutes before the start of experimentation. PSS was aerated with a mixture of 95% $O_2$-5% $CO_2$; the composition was as follows (in mM): 130 NaCl, 4.7 KCl, 1.18 $KH_2PO_4$, 1.17 $MgSO_4.7H_2O$, 14.9 $NaHCO_3$, 1.6 $CaCl_2H_2O$, 5.5 dextrose, and 0.03 $CaNa_2$-EDTA 0.03 (pH 7.30).

The blood vessel segments were pretreated, for 30 minutes, either with a 1:1000 dilution of ethanol, or with 10 μM tamoxifen (in ethanol, from Sigma Chemical, St. Louis, Mo.).

Sensitivity was quantified by measuring the 50% effective dose of agonist (ED50) by linear regression following log transformation of the agonist concentration and logit transformation of the response data. Data were expressed as a percentage of the maximal response of each ring to the agonist.

Example 2

Tamoxifen Normalizes NE Induced VSM Sensitivity

Figure 2:
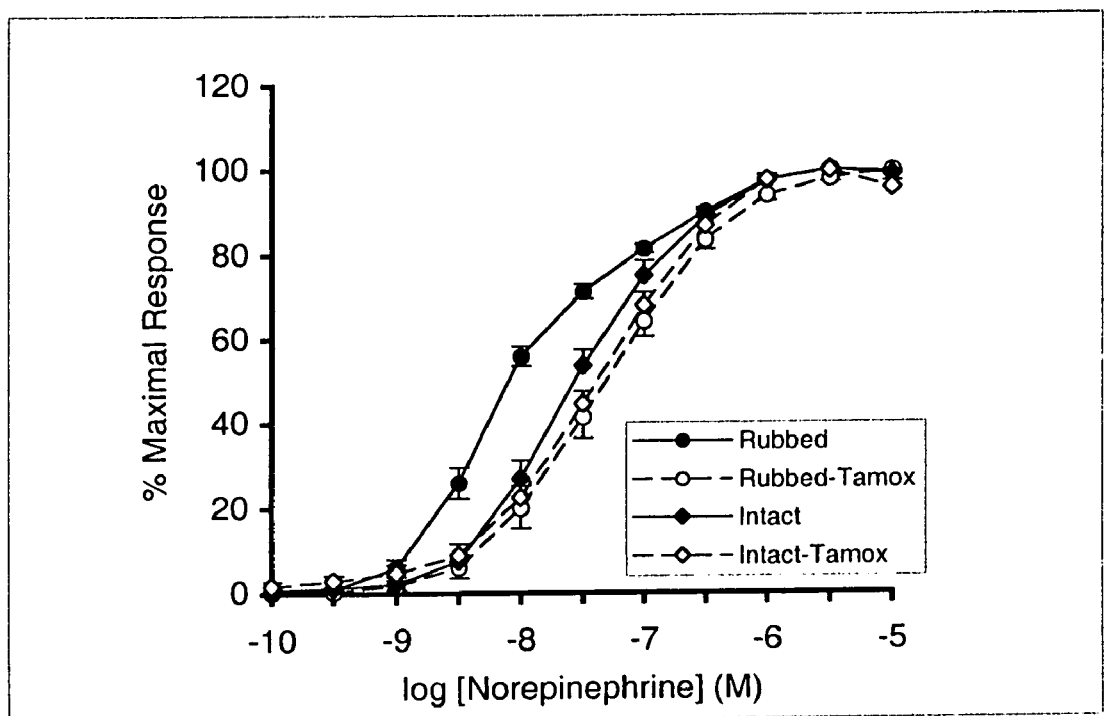
FIG. 2: Tamoxifen shifts the dose-response curve of NE back to the right in endothelially-compromised vascular smooth muscle, and normalizes the contractile responses, so that there is no longer a significant difference in sensitivity between intact and compromised vessels.

1. Intact and denuded aortic blood vessel segments were prepared, mounted as described in Example 1.
2. Blood vessel segments were pretreated with tamoxifen was measured as described in Example 1. Control blood vessel segments were pretreated with ethanol at the same concentration used to dissolve the tamoxifen.
3. Aliquots of NE (Sigma Chemical, St. Louis, Mo.), which had been dissolved directly into aqueous solution was applied to the vessel segments at concentrations between $10^{-10}$ and $10^{-5}$M, and the contractile response measured as described above. The results are shown in FIG. 2. In general, the results show that tamoxifen treated denuded blood vessel segments were similar in contractility to intact blood vessels, whereas denuded blood vessel segments which were not treated with tamoxifen were more sensitive to NE than intact blood vessels. The $ED_{50}$ values calculated for NE were as follows: Denuded blood vessel segments=$1.55\pm0.19\times10-8$M (control), $5.85\pm1.51\times10^{-8}$M (tamoxifen, $p\leq0.05$); Intact blood vessel segments=$3.41\pm0.72\times10^{-8}$M (control), $3.28\pm0.41\times10^{-8}$M (tamoxifen).

Example 3

Tamoxifen Normalizes KCl Induced VSM Sensitivity

Figure 3:
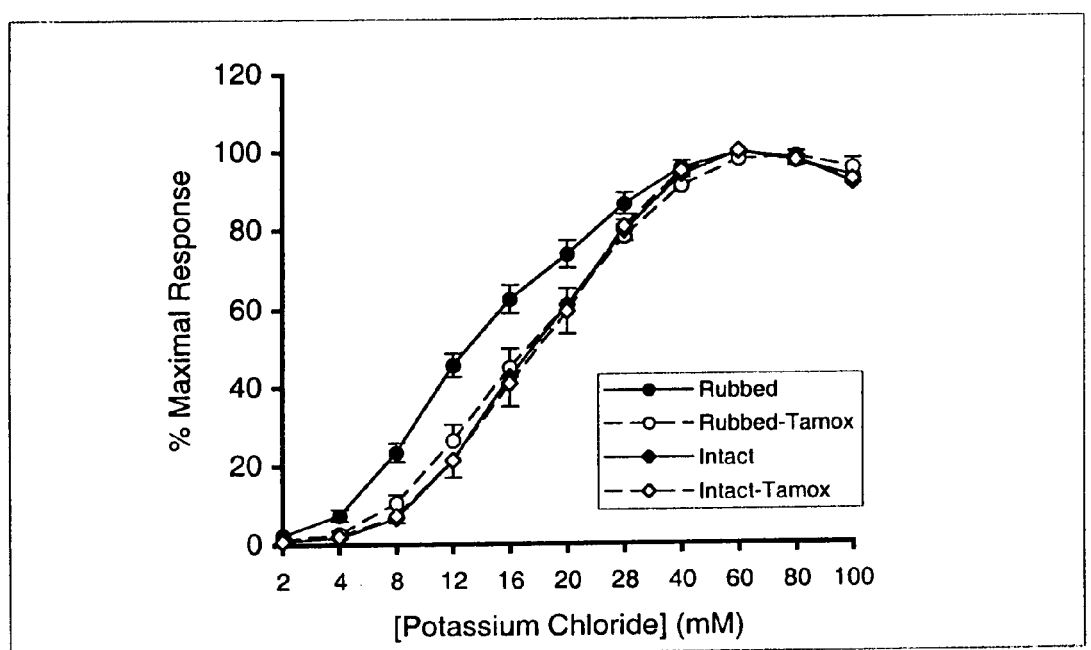
FIG. 3: Tamoxifen treatment corrects the increase in vascular smooth muscle sensitivity to KCl associated with mechanical removal of the endothelium.

1. Intact and denuded aortic blood vessel segments were prepared and mounted as described in Example 1.
2. Test blood vessel segments were pretreated with tamoxifen as described in Example 1. Control blood vessel segments were pretreated with ethanol at the same concentration used to dissolve the tamoxifen.
3. KCl (Sigma Chemical, St. Louis, Mo.), was applied to the vessels at 2, 4, 8, 12, 16, 20, 28, 40, 60, 80, and 100 mM concentrations, and the contractile response measured as described above. The results are shown in FIG. 3. In general, the results show that tamoxifen-treated denuded blood vessel segments were similar in contractility to intact blood vessels, whereas denuded blood vessel segments which were not treated with tamoxifen were more sensitive to KCl than intact blood vessels. The $ED_{50}$ values calculated for KCl were as follows: Denuded blood vessel segments=$12.3\pm0.70$ mM (control), $16.9\pm1.4$ mM (tamoxifen, $p\leq0.05$); Intact blood vessel segments=$17.6\pm1.6$ mM (control), $17.5\pm1.6$ mM (tamoxifen).

Example 4

Estrogen Receptors not Responsible for Tamoxifen Normalization of Agonist Sensitivity Electrophysiology. Chloride ion currents were measured from cultured human aortic and coronary vascular smooth muscle cells at room temperature (22–24 C) using standard whole-cell voltage-clamp techniques (Hamill et al., 1981; Lamb et al., 1994) and an Axopatch 200B patch-clamp amplifier driven by pClamp software (Axon Instruments). The hypotonic (250 mOsm/kg by freezing point depression) bath solution contained (mM): NaCl 125, $MgCl_2$ 2.5, $CaCl_2$ 2.5, HEPES 10, Ph 7.2. Isotonic bath solution had the same ionic composition as the hypotonic solution except that the osmolality was adjusted to 300 mOsm/kg by adding mannitol. Pipette solution contained (mM): N'-methyl-D-glucamine chloride (NMDG-Cl) 135, EGTA 2, Mg-ATP 5, HEPES 10, pH 7.2 with osmolality adjusted to 300 mOsm/kg by adding mannitol. Thus, the chloride equilibrium potential remained 0 mV under both isotonic and hypotonic conditions. All components of the buffer solutions were obtained from Sigma. Pipette resistances were 3–5 MOhms.

Patch-clamp recording of the swelling-induced Cl ion current from cultured vascular smooth muscle cells revealed that this current is inhibited by tamoxifen, using methods described above. In contrast, β-estradiol (E, $10^{-7}$ M) did not inhibit but rather increased the swelling-induced Cl current (ICl, pA) seen under hypotonic conditions at +120 mV (hypotonic only=$1451\pm495$ pA, hypotonic plus estradiol=$3513\pm856$, n=5). This result suggests that the ability of Tamoxifen to inhibit this current cannot be accounted for by tamoxifen-induced activation of estrogen receptors.

Example 5

Protein Kinase C Inhibition not Responsible for Tamoxifen Normalization of Agonist Sensitivity The methods as described in Example 4 were used in this example as well. The protein kinase C (PKC) inhibitor H-7 ($10^{-5}$ M) increased the swelling-induced chloride current above the level induced by hypotonic buffer alone. However, tamoxifen still inhibited the swelling-induced current in the presence of H-7 (hypotonic=$1204\pm313$ pA, hypotonic+H7+tamoxifen=$878\pm493$ pA, n=3). This result suggests that activation of PKC is not the mechanism by which tamoxifen inhibits the swelling-induced chloride current.

What is claimed is:

1. A method to normalize the contractile response of vasculature in response to a vasoconstrictor agonist in a patient in need of such normalization, the vasculature comprising a vascular smooth muscle cell layer and a compromised endothelial cell layer, wherein the method comprises administering a pharmaceutically effective amount of a CLC3 blocker, or a pharmaceutically acceptable salt thereof, and wherein the vasoconstrictor agonist is norepinephrine.

2. A method of claim 1, wherein the CLC3 blocker is a compound of Formula I

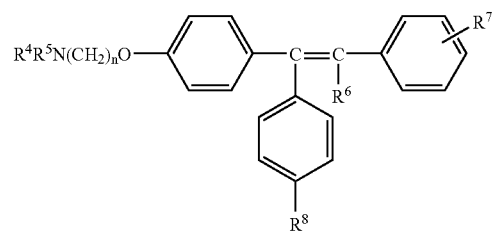

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof.

3. A method of claim 2, wherein the compound administered is 1-p-β-dimethylaminoethoxyphenyl-trans-1,2-diphenylbut-1-ene, or a pharmaceutically acceptable salt thereof.

4. A method of claim 2, wherein the patient has diabetes.

5. A method of claim 2, wherein the patient has had a surgical procedure.

6. A method of claim 2, wherein the patient has hypertension.

7. A method of claim 2, wherein the patient has coronary artery disease.

8. A method of claim 2, which further comprises administering a pharmaceutically-effective compound selected from the group consisting of: an anti-diabetes agent; an anti-hypertension agent; an anti-coronary artery disease agent; and an anti-restenosis agent.

* * * * *